United States Patent [19]
Sanou et al.

[11] Patent Number: 5,874,401
[45] Date of Patent: *Feb. 23, 1999

[54] CEDAR POLLEN PROTEIN AND USE THEREOF IN TREATING, PREVENTING, AND DIAGNOSING POLLENOSIS

[75] Inventors: Osamu Sanou; Katsuhiko Hino; Masashi Kurimoto, all of Okayama, Japan

[73] Assignee: Kabushiki Kaisha Hayashibara Seibutsu Kagaku Kenkyujo, Okayama, Japan

[*] Notice: This patent issued on a continued prosecution application filed under 37 CFR 1.53(d), and is subject to the twenty year patent term provisions of 35 U.S.C. 154(a)(2).

[21] Appl. No.: 773,008

[22] Filed: Dec. 24, 1996

Related U.S. Application Data

[63] Continuation of Ser. No. 354,815, Dec. 8, 1994, abandoned.

[30] Foreign Application Priority Data

Dec. 27, 1993 [JP] Japan .................................. 5-347017

[51] Int. Cl.⁶ .......................... A61K 38/16; A61K 39/36; A61K 49/00; C07K 14/415
[52] U.S. Cl. .......................... 514/8; 424/9.81; 424/185.1; 424/276.1; 530/379; 530/395
[58] Field of Search ............................... 514/8; 530/379, 530/395, 423, 424; 424/195.1, 185.1, 193.1, 275.1, 276.1, 9.81

[56] References Cited

U.S. PATENT DOCUMENTS

| | | | |
|---|---|---|---|
| 4,666,855 | 5/1987 | Yang et al. | 436/89 |
| 5,547,928 | 8/1996 | Wu et al. | 514/2 |

FOREIGN PATENT DOCUMENTS

| | | |
|---|---|---|
| 0308147 | 3/1989 | European Pat. Off. . |
| 0416816 | 3/1991 | European Pat. Off. . |
| 156926 | 6/1989 | Japan . |
| 93730 | 4/1991 | Japan . |
| 9301213 | 1/1993 | WIPO . |
| 1560 | 1/1994 | WIPO . |

OTHER PUBLICATIONS

J. Allergy Clin. Immunol., vol. 82, No. 3, Part 1, issued Sep. 1988, Miyazawa et al, "A reverse–sandwich ELISA for IgG . . . ", pp. 407–413.
Neurath et al, The Proteins, 3rd ed. New York: Academic Press, 1975, vol. 1, pp. 180, 191.
Database WPI, Section Ch, Week 8832, Derwent Publication Ltd., London, GB; Class B04, AN 88–224232, JP63159324 (Lion Corp), 2 Jul. 1988.
Allergy, Japanese Journal Allergology, vol.42, No.6, pp. 738–747, 1993.
Yasueda et al, Isolation and Partial Characterization . . . Pollen, J. Allergy Clin. Immunol., vol.71, No.1, part1, pp. 77–86 (1983).
Taniai et al, N–Terminal Amino Acid Sequence . . . Pollen, FEBS Letters, vol.239, No.2, pp. 329–332, Nov. 1988.
Sakaguchi et al, Identification of the Second Major . . . Pollen, Allergy, vol.45, pp. 309–312, 1990.
Laemmli, Cleavage of Structural Protein . . . T4, Nature, vol.227, pp. 680–685, Aug. 15, 1970.
Yoshitake et al, Mild and Efficient Conjugation of Rabbit Fab . . . Immunoassay, J.Biochem., vol.92, pp. 1413–1424, 1982.
Mota et al, Homologous and Heterologous Passive . . . Immunization, Life Sciences, vol.8 part2, pp.813–820, 1969.
Rinsho Meneki, Clinical Immunology, vol.20, No.11, pp. 1047–1052, 1988. Abstract.
Takahasi et al, Japanese Journal of Allerology, vol.43, No.2, pp. 97–100, 1994. Abstract.
Sawatani et al, Enzym–Linked Immunosorbent Assay, Japanese Journal of Allergology, vol.43, No.3, pp. 467–473, 1994. Abstract.
Sakaguchi et al, Measurement of Serum IgE Antibodies against Japanese . . . pollinosis, J.Med.Primatol, vol.21, pp. 323–327, 1992. Abstract.
Usui et al, Biological and Immunological Properties . . . Conjugate, Trends in Glycoscience and Glycotechnology, vol.4, No.20, pp. 525–532, Nov. 1992. Abstract.
Usui et al, Biological and Immunological Properties . . . Conjugate, Internal Archives of Allergy and Applied Immunology, Reprint vol.91, No.1, pp. 74–79, 1990. Abstract.
Taniguichi et al, Biological and Immunological Properties . . . Conjugate, International Archives of Allergy and Applied Immunology, vol.89, pp. 136–142, 1989. Abstract.
Taniai et al, Epitopes on Cry j I and Cry j II for the Human IgE . . . Pollen, Molecular Immunology vol.30, No.2, pp. 183–189, 1993. Abstract.
Kawashima et al, Antigenic Analyses of Sugi Basic . . . Cry j I, International Archives of Allergy and Immunology, vol.98, pp. 118–126, 1992. Abstract.
Kawashima et al, Antigenic Analyses of Sugi Basic . . . Molecules, International Archives of Allergy and Immunology vol.98, pp. 110–117, 1992. Abstract.

*Primary Examiner*—Jeffrey E. Russel
*Attorney, Agent, or Firm*—Browdy and Neimark

[57] ABSTRACT

A protein having a molecular weight of 44,000–54,000 daltons, isoelectric point of 8.5–9.2 and specific sugar chain is prepared from a cedar pollen. The protein induces pollenosis and can be suitably used as desensitization agent because it induces immunoglobulin antibody which is effective for desensitization, but does not substantially induce immunoglobulin E antibody, a major factor causative of side effects including anaphylaxis shock. Therefore, the protein can be advantageously used in the treatment, prevention and/or diagnosis of pollenosis.

16 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

Asp Asn Pro Ile Asp Ser
  1               5

( 2 ) INFORMATION FOR SEQ ID NO:2:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

Ala Ile Asn Ile Phe Asn
  1               5

( 2 ) INFORMATION FOR SEQ ID NO:3:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Asn Gly Asn Ala Thr Pro Gln Leu Thr Lys Asn Ala Gly Val Leu Thr
  1               5                   10                  15

Cys Ser Leu Ser Lys Arg Cys
                  20

( 2 ) INFORMATION FOR SEQ ID NO:4:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Glu Ala Phe Asn Val Glu Asn Gly Xaa Ala Thr Pro Gln Leu Thr Lys
  1               5                   10                  15

( 2 ) INFORMATION FOR SEQ ID NO:5:

( i ) SEQUENCE CHARACTERISTICS:
    ( A ) LENGTH: 41 amino acids
    ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:5:

```
Thr Ala Thr Asn Ile Trp Ile Asp His Asn Ser Phe Ser Xaa Ser Ser
 1           5                  10                  15
Asp Gly Leu Val Asp Val Thr Leu Thr Ser Thr Gly Val Thr Ile Ser
            20              25                  30
Asn Asn Leu Phe Phe Asn His His Lys
         35              40
```

CEDAR POLLEN PROTEIN AND USE THEREOF IN TREATING, PREVENTING, AND DIAGNOSING POLLENOSIS

This application is a continuation of application Ser. No. 08/354,815 filed Dec. 8, 1994, now abandoned.

BACKGROUND OF THE INVENTION

1. Field of the Invention

The present invention relates to a novel protein which induces pollenosis and to a process for producing the same, as well as to uses thereof as a desensitizing agent for treating, preventing and/or diagnosing pollenosis.

2. Description of the Prior Art

For more than ten years, the number of patients who complain about rhinitis and conjunctivitis due to pollenosis in early spring, has been increasing in Japan. Pollenosis frequently receives much publicity from the press because the number of cases of pollenosis is significantly increasing and because it occurs in early spring at which a variety of events, festivals and the like are held. Therefore, pollenosis has become a problem of public health which could not be ignored.

It is said that pollenosis is a types of allergic reaction which is mainly induced by allergens present in cedar pollens (the wording "cedar" as referred to in the invention means *Cryptomeria japonica* and plants of the genus Cedrus), i.e., cedar pollen allergens. The invasion of such an allergen, dispersed in the air, into the body resulted in the formation of immunoglobulin E antibody specific to the allergen. When the body being in such condition is re-invaded by cedar pollens, both cedar pollen allergens contained in the invaded pollens and the already formed immunoglobulin E antibody in the body induce an immunoreaction to cause an allergic symptom.

Until now, it is known that at least 2 different types of allergens with different antigenicities are contained in cedar pollens. The one is an allergen, which is now called "*Cry j* I", as reported by H. YASUEDA et al. in *Journal of Allergy and Clinical Immunology*, Vol.71, No.1, Part 1, pp.77–86 (1983), and the other is an allergen, which is now called "*Cry j* II", as reported by M. TANIAI et al. in *FEBS LETTERS*, Vol.239, No.2, pp.329–332 (1988) or by M. SAKAGUCHI et al. in *Allergy*, No.45, pp.309–312 (1990). Usually, cedar pollens contain *Cry j* I and *Cry j* II in a weight ratio of about 50:1 to 5:1, and most of the sera collected from patients with pollenosis are said to react with both *Cry j* I and *Cry j* II. M. SAWATANI et al. reported in *Japanese Journal of Allergology*, Vol.42, No.6, pp.738–747 (1993) that *Cry j* II exerts the same level of antigenicity as that exerted by *Cry j* I when assayed on the intradermal test (IT) and radioallergosorbent test (RAST).

As described above, several cedar pollen allergens have been isolated and their properties and characteristics have to some extent been assayed. Because of this it may be possible to treat and/or prevent pollenosis by administering to a human a purified preparation of a cedar pollen allergen for desensitization. Recently, desensitization agents for such a purpose have been proposed: For example, Japanese Patent Laid-Open Nos.156,926/89 and 93,730/91 propose a method to administer to a human a conjugate desensitization agent prepared by conjugating a polysaccharide such as pullulan to an allergen having a partial amino acid sequence of Asp-Asn-Pro-Ile-Asp-Ser-(SEQ ID NO:1) or Ala-Ile-Asn-Ile-Phe-Asn-(SEQ ID NO:2) at the N-terminal. Since pollenosis-inducing allergens are not restricted to *Cry j* I and *Cry j* II, other pollenosis-related allergens should be urgently isolated and assayed for their properties and characteristics to establish an accurate diagnosis and an effective desensitization-therapy of pollenosis.

SUMMARY OF THE INVENTION

In view of the foregoing, the present invention was made and one object of the present invention is to provide a novel protein which induces pollenosis.

It is a further object of the present invention to provide a method to prepare the protein.

It is yet another object of the present invention to use the protein as desensitization agent.

The first object of the present invention is attained by a protein having the following physicochemical properties (hereinafter designated as "protein"). In the specification, amino acids, sugars, their coupling modes, etc. may be abbreviated and expressed in accordance with the abbreviations specified by International Union of Pure and Applied Chemistry (IUPAC):

(1) Molecular weight
   44,000–54,000 daltons on sodium dodecyl polyacrylamide gel electrophoresis (SDS-PAGE);

(2) Isoelectric point (pI)
   8.5–9.2 on isoelectrophoresis;

(3) Partial amino acid sequence containing the C-terminal
   Possessing a partial amino acid sequence containing the C-terminal as shown by -Asn-Gly-Asn-Ala-Thr-Pro-Gln-Leu-Thr-Lys-Asn-Ala-Gly-Val-Leu-Thr-Cys-Ser-Leu-Ser-Lys-Arg-Cys (SEQ ID NO:3);

(4) Sugar content
   Containing about 5–20% by weight of a sugar chain having a chemical structure in the molecule as shown by the following chemical formula 1. Where "X", "X'" and "X''" represent hydroxyl group or Fucα1, and "Y" and "Y'" represent hydroxyl group or Galβ1. Chemical formula 1:

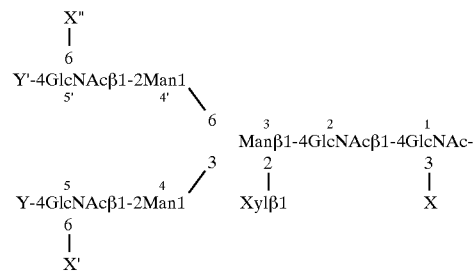

(5) Ultraviolet absorption spectrum
   Exhibiting the maximum absorption spectrum at a wave length around 280 nm;

(6) Solubility in solvent
   Soluble in water, physiological saline and phosphate buffer;

(7) Biological activity
   Attaching to immunoglobulin E antibody collected from blood of a patient with pollenosis. Inducing pollenosis; and (8) Stability
   Being inactivated in an aqueous solution (pH 7.2) when incubated at 100° C. for 10 minutes.
   Substantially not losing its activity in an aqueous solution (pH 7.2) even when allowed to stand at 4° C. for one month.

The second object of the present invention is attained by extracting a cedar pollen with an aqueous solvent, and recovering a protein from the resultant extract.

The third object of the present invention is attained by a desensitization agent which contains the protein as an effective ingredient.

DETAILED DESCRIPTION OF THE INVENTION

The protein according to the present invention is a novel substance having specific properties which are entirely different from those of conventional allergens present in cedar pollens.

The present process makes it possible to produce the protein from cedar pollens in a relatively-high yield.

The desensitization agent according to the present invention exerts a considerably-high desensitization activity when administered to mammals including humans.

The present invention relates to a novel protein which induces pollenosis. During the research of cedar pollen allergens, we found that there exists an unknown allergen in cedar pollens. We isolated such allergen by combining column chromatography as the main technique with other purification methods, and investigated the properties and characteristics to reveal that the protein has different properties and characteristics from those of conventional allergens of cedar pollens.

The following experiments explain the specific properties and characteristics of the present protein:

EXPERIMENT 1
Purification of protein

One part by weight of a cedar pollen collected from a male flower of "omote-sugi" or Cryptomeria japonica, grown in Chiba, Japan, was suspended in and extracted with about 16 parts by weight of an aqueous solution of 0.125M sodium hydrogen carbonate (pH 8.2) while stirring at 4° C. for one hour, followed by centrifuging the resultant extract to obtain a supernatant. The sediment was treated similarly as above to obtain a supernatant which was then pooled with the above supernatant. To the solution was added 0.1 w/v % "CETAVLON", hexadecyl-trimethylammonium bromide, commercialized by Sigma, Chemicals Co., Louis, USA, and the mixture was centrifuged to obtain a supernatant which was then mixed with ammonium sulfate to give a saturation degree of 80 w/v % to salt out proteinaceous components. The resultant sediment was dialyzed against 50 mM Tris-HCl buffer (pH 7.8) for 10 hours, filtered and fed to a column packed with DEAE-SEPHADEX® which had been previously equilibrated with 50 mM Tris-HCl buffer (pH 7.8), followed by recovering non-adsorbed fractions by feeding 50 mM Tris-HCl buffer (pH 7.8) to the column.

The non-adsorbed fractions were pooled, adjusted to pH 5.0 by the addition of acetic acid, and fed to a column packed with CM-SEPHADEX® which had been previously equilibrated with 10 mM acetate buffer (pH 5.0). The column was washed by feeding thereto 10 mM acetate buffer (pH 5.0), and fed with an eluant of 0.3M sodium chloride and 0.1M phosphate buffer (pH 7.0) to elute proteinaceous components. The fractions containing the proteinaceous components were pooled and fed to a column packed with "MONO-S" which had been previously equilibrated with 10 mM phosphate buffer (pH 5.0), and the column was fed with a linear gradient buffer of sodium chloride increasing from 0M to 0.5M in 10 mM Tris-HCl buffer (pH 7.0) to obtain the desired protein contained in fractions with a concentration of 0.1–0.3M sodium chloride. The fractions were pooled, concentrated in the usual manner, lyophilized and used in the following experiments. The yield of the protein was about 0.02% of the material cedar pollen, on a dry solid basis (d.s.b.).

EXPERIMENT 2
Physicochemical properties of protein

In this experiment the physicochemical properties of purified protein obtained in Experiment 1 were studied.

EXPERIMENT 2-1
Molecular weight

In accordance with the method as reported by U. K. Lemuli in *Nature*, Vol.227, pp.680–685 (1970), the purified protein was assayed on SDS-PAGE to show a major band in a position corresponding to 44,000–54,000 daltons. The molecular markers used in this experiment were calf serum albumin with a molecular weight of 67,000 daltons, ovalbumin with a molecular weight of 45,000, carbonic anhydrolase with a molecular weight of 30,000 daltons, chymotrypsinogen A with a molecular weight of 25,000 daltons, and cytochrome C with a molecular weight of 12,400 daltons.

A fraction corresponding to 44,000–54,000 daltons was transferred from the gel to a nitrocellulose membrane, and treated with an antibody of anti-cedar pollen allergen derived from mice and an anti-mouse immunoglobulin antibody, derived from goats, labelled with peroxidase from horseradish, to exhibit a distinct immunostaining. The result indicates that the protein is a cedar pollen allergen.

EXPERIMENT 2-2
Isoelectric point

The isoelectric point of the purified protein in Experiment 1 was 8.5–9.2 when assayed on isoelectrophoresis.

EXPERIMENT 2-3
Partial amino acid sequence containing the C-terminal

Four hundred pg of the purified protein in Experiment 1 was placed in a reaction tube, and dissolved in 300 $\mu$l of 6M guanidine hydrochloride and 10 mM EDTA in 0.5M Tris-HCl buffer (pH 8.5). The tube was filled with nitrogen gas, and the contents were mixed with adequate amounts of ethyleneimmine and tri-n-butylphosphine. The resultant peptide components were allowed to stand in a light-shielded place overnight to effect aminoethylation. The reaction mixture thus obtained was dialyzed against distilled water, and the dialyzed solution was recovered, lyophilized, dissolved in 300 $\mu$l of 0.05M acetate buffer (pH 4.0), mixed with 15 $\mu$g V8 protease, and incubated at 37° C. for 48 hours. Thereafter, the resultant mixture was heated at about 100° C. for 5 min to suspend the enzymatic reaction, and fed to a column packed with anhydrotrypsine agarose which had been previously equilibrated with 0.05M acetate buffer (pH 5.0) containing 0.02M calcium chloride, followed by eluting from the column the peptide components adsorbed on the agarose with 0.1M formic acid.

From the eluate, fractions containing the peptide components were recovered, concentrated, fed to "218TP54", a column for reverse-phase high-performance liquid chromatography commercialized by Vydac, California, USA, which had been previously equilibrated with 0.1 v/v % aqueous trifluoroacetate solution, and eluted with water-soluble acetonitrile containing 0.1 v/v % trifluoroacetate at a flow rate of 0.5 ml/min while the concentration of acetonitrile was increasing at a rate of one v/v % per minute and monitoring the eluate at a wave length of 214 nm. From the resultant eluate the peptide components were recovered, concentrated and analyzed for their amino acid sequences on "MODEL 473A", an amino acid sequencer commercialized by Applied Biosystems, Inc., Foster City, USA, to reveal that the protein has a partial amino acid sequence as shown by -Asn-Gly-Asn-Ala-Thr-Pro-Gln-Leu-Thr-Lys-Asn-Ala-Gly-Val-Leu-Thr-Cys-Ser-Leu-Ser-Lys-Arg-Cys (SEQ ID NO:3) at its C-terminal.

EXPERIMENT 2-4

Determination of sugar content and structure of sugar chain

This experiment is to reveal the sugar content of the present protein and the structure of sugar chains as well as the position of their linkages.

EXPERIMENT 2-4(a)

Sugar content

About 5–20 µg sugars were detected in 100 µg of the purified protein in Experiment 1 by conventional analysis using mannose as a standard substance. The result shows that the protein contains about 5–20 w/w % sugars, d.s.b.

EXPERIMENT 2-4(b)

Sugar component and position of linkage of sugar chain

One mg of the purified protein in Experiment 1 was placed in a reaction tube, admixed with and dissolved to homogeneity in 300 µl of 0.5M Tris-HCl buffer (pH 8.5) containing 6M guanidine and 10 mM EDTA, and further admixed with one µl 4-vinylpyridine and 2 µl tri-n-butylphosphine after the tube was filled with nitrogen gas, followed by allowing the resultant mixture to stand for 24 hours under dark conditions to effect pyridylethylation. Thereafter, the reaction mixture was dialyzed against distilled water for 10 hours, and the dialyzed solution was recovered, concentrated, lyophilized, dissolved in 300 µl of 0.2M ammonium acetate (pH 8.6), admixed with 15 µg trypsin, and incubated at 37° C. for 17 hours.

The resultant trypsin hydrolysates were fed to a column of "218TP54", a column for reverse-phase high-performance liquid chromatography, commercialized by Vydac, California, USA, which had been previously equilibrated with 0.1 v/v % trifluoroacetate in distilled water, and eluted from the column with an acetonitrile solution containing one v/v % trifluoroacetate at a flow rate of 0.5 ml/min while the concentration of acetonitrile was increasing at a rate of one v/v % per minute. The eluate was monitored at a wave length of 214 nm. From the eluate, fractions containing peptide fragments were recovered, pooled, placed in a test tube, and analyzed for the presence of neutral sugars by the resorcinol-sulfuric acid reaction to reveal that neutral sugars were contained in 2 different types of peptides. The one was named "peptide fragment A", and the other was named "peptide fragment B", and they were analyzed for their amino acid sequences on "MODEL 473A", an amino acid sequencer commercialized by Applied Biosystems, Inc., Foster City, USA.

As a result, the peptide fragments A and B have the following amino acid sequences as shown in Table 1:

TABLE 1

Peptide fragment A:

Glu-Ala-Phe-Asn-Val-Glu-Asn-Gly-Xaa-Ala-Thr-Pro-Gln-Leu-Thr-Lys (SEQ ID NO: 4)

Peptide fragment B:

Thr-Ala-Thr-Asn-Ile-Trp-Ile-Asp-His-Asn-Ser-Phe-Ser-Xaa-Ser-Ser-Asp-Gly-Leu-Val-Asp-Val-Thr-Leu-Thr-Ser-Thr-Gly-Val-Thr-Ile-Ser-Asn-Asn-Leu-Phe-Phe-Asn-His-His-Lys (SEQ ID NO: 5)

In order to identify the amino acid residue as indicated by "Xaa" in the amino acid sequences in Table 1, a portion of peptide fragment A or B was placed in a test tube, admixed with an adequate amount of 6N hydrochloride, and hydrolyzed by incubating it in vacuo at 110° C. for 20 hours. After completion of the hydrolysis, the resultant hydrolysates were in the usual manner analyzed for their amino acid components on "MODEL 6300", an amino acid analyzer commercialized by Beckman Instruments, Inc., California, USA, to obtain the results shown in Table 2:

TABLE 2

| Amino acid residue | Amino acid component (number of residue) | |
|---|---|---|
| | Peptide fragment A | Peptide fragment B |
| Asx | 2.5(3) | 9.0(9) |
| Thr | 1.6(2) | 5.5(6) |
| Ser | 0.4(0) | 5.9(6) |
| Glx | 2.6(3) | 0.0(0) |
| Pro | 0.8(1) | 0.0(0) |
| Gly | 1.3(1) | 3.5(2) |
| Ala | 1.7(2) | 1.3(1) |
| Cys | 0.0(0) | 0.0(0) |
| Val | 0.9(1) | 2.9(3) |
| Met | 0.0(0) | 0.0(0) |
| Ile | 0.0(0) | 2.7(2) |
| Leu | 1.1(1) | 2.7(3) |
| Tyr | 0.0(0) | 0.0(0) |
| Phe | 0.4(1) | 2.6(3) |
| His | 0.0(0) | 2.8(3) |
| Lys | 1.0(1) | 1.4(1) |
| Arg | 0.0(0) | 0.0(0) |

Note: In the table each numeral in each parenthesis is an approximate integer.

The comparison of the amino acid sequences as shown in Table 1 and the amino acid components as shown in Table 2 suggests that the unidentified amino acid "Xaa" in the amino acid sequence of Table 1 might clearly be "Asn" to which a sugar chain is attached.

EXPERIMENT 2-4(c)

Isolation of sugar chain and its sugar component

One hundred and fifty mg of the purified protein in Experiment 1 was placed in a container, admixed with and dissolved in a small amount of distilled water, and dialyzed against distilled water for 10 hours. The dialyzed solution was recovered, adjusted to pH 2 by the addition of hydrochloride, admixed with 1.5 mg pepsin, and incubated at 37° C. for 18 hours to cut the peptide bonds in the protein. The reaction mixture was lyophilized, dissolved in 0.1M citric acid-phosphate buffer (pH 5.5), admixed with 10 m units of "GLYCOPEPTIDASE" commercialized by Seikagaku-Kogyo Co., Ltd., Tokyo, Japan, and incubated at 37° C. for 16 hours to release sugar chains from peptide fragments.

Thereafter, the reaction mixture was fed to a column packed with "BIO-GEL P-4", a gel of Bio-Rad Laboratories Inc., Brussels, Belgium, which had been treated with distilled water to form a gel, and the column was then fed with distilled water, followed by collecting the eluate in 5 ml fractions and determining the presence of neutral sugars by the resorcinol-sulfuric acid reaction. A portion of a fraction, in which a neutral sugar had been detected, was placed in a container, lyophilized, dissolved in 60 µl of 4N hydrochloride containing 0.08 g 2-aminopyridine, incubated at 100° C. for 13 min, admixed with 10 mg sodium cyanotrihydroborate dissolved in 6 µl of distilled water, and further incubated at 90° C. for 18 hours. Finally, the reaction mixture was purified on a column packed with "TSKgel TOYOPEARL® HW-40F", a gel for chromatography commercialized by Tosoh Corporation, Tokyo, Japan, which had been previously equilibrated with 0.01M ammonium acetate buffer (pH 6.2), to obtain a fluorescent-labelled sugar-chain free of intact reaction reagents.

The fluorescent-labelled sugar-chain was fed to a column packed with "TSKgel Amido-80", a gel for high-performance liquid chromatography commercialized by Tosoh Corporation, Tokyo, Japan, which had been previously equilibrated with a solution containing 3 v/v % acetic acid-triethylamine buffer (pH 7.3) and acetonitrile in a ratio of 35:65 by volume, and eluted from the column by feeding thereto a linear gradient eluant of 3 v/v % acetic acid-triethylamine buffer and acetonitrile while their volume ratio was increasing to 50:50 in a period of 50 min at a flow rate of one ml/min, followed by the elution of 4 different sugar-chains about 18, 22, 27 and 35 min after the initiation of the elution. The sugar chains were named "sugar-chain A", "sugar-chain B", "sugar-chain C" and "sugar-chain D" and subjected to the following analysis for sugar components. The sugar-chains A and C were detected in a relatively-high level, while the contents of the sugar-chains B and D were relatively-low.

The sugar-chain A, B, C or D was lyophilized, admixed with an excessive amount of 4M trifluoro acetate, and hydrolyzed in vacuo at 100° C. for 3 hours. The hydrolysates were dissolved in an adequate amount of pyridine-methanol-distilled water (3:6:2 by volume), admixed with an excess amount of anhydrous acetic acid, and allowed to stand at ambient temperature for 30 min to effect acetylation. The reaction mixture was recovered, lyophilized, dissolved in 50 μl of 4N hydrochloride containing 66 mg 2-aminopyridine, heated at 100° C. for 13 min, admixed with 5 μl of distilled water containing 0.8 mg sodium cyanotrihydroborate, and incubated at 90° C. for 18 hours. Thereafter, the reaction mixture was fed to a column packed with "TSKgel G2000PW", a gel for high-performance liquid chromatography commercialized by Tosoh Corporation, Tokyo, Japan, which had been equilibrated with 20 mM ammonium acetate buffer (pH 7.5), and the column was then fed with a fresh preparation of the same buffer at a flow rate of 0.6 ml/min to remove intact reaction reagents. The eluate containing saccharides in mixture was fed to a column packed with "TSKgel Sugar AX-I", a gel for high-performance liquid chromatography, which had been previously equilibrated with 0.5M borate buffer (pH 8.7) containing 15 v/v % acetonitrile. The column was then fed with a fresh preparation of the same buffer at 60° C. and at a flow rate of 0.4 ml/min, followed by analyzing the types and contents of sugars which consist the sugar chains. The results were as shown in Table 3:

TABLE 3

| Sugar chain | Sugar component | | | | |
|---|---|---|---|---|---|
| | Gal | Fuc | Man | Xyl | GlcNAc |
| Sugar chain A | 0.0 | 1.0 | 3.0 | 1.2 | 3.8 |
| Sugar chain B | 1.0 | 1.0 | 3.0 | 1.1 | 3.5 |
| Sugar chain C | 1.1 | 2.1 | 3.0 | 0.8 | 4.1 |
| Sugar chain D | 2.1 | 3.1 | 3.0 | 0.8 | 3.8 |

Note: In the table each numeral represents a relative value provided the value of Man, i.e. mannose, is 3.0.

The results in Table 3 indicate that the sugar chains A to D attached to the present protein consist of 0 to 2 galactose residues (Gal), 1 to 3 fucose residues (Fuc), 3 mannose residues (Man), one xylose residue (Xyl) and 4 N-acetylglucosamine residues (GlcNAc), and at least one of these sugar chains is attach ed to the present protein.

EXPERIMENT 2-4(d)

Determination of sugar-chain structure

The sugar chains A to D, isolated in Experiment 2-4(c), were placed in containers, lyophilized, dissolved in a small amount of heavy water, and lyophilized. The above procedure was repeated thrice for each sugar chain to replace dissociative hydrogens in each sugar chain with deuterium. Thereafter, the resultant was analyzed on a 500-MHz $^1$H NMR (nuclear magnetic resonance) spectroscope, commercialized by JEOL U.S.A., Inc., Peabody, Mass., USA, to analyze the chemical shifts of anomeric- and methyl-protons in each sugar chain at 30° C. in heavy water. The results are as shown in Table 4.

The present inventors investigated conventionally known sugar chains which exhibit similar chemical shifts to those of the aforesaid sugar chains of A to D, and found that, as shown in *Biochemistry*, Vol.25, pp.388–395 (1986) reported by N. TAKAHASHI et al., the sugar chains c, e and f attaching to laccase, i.e. an enzyme derived from sycamore (*Acer pseudoplatanus* L.), exhibits nearly the same chemical shifts as those exhibited by the sugar chains A to D when assayed on 400-MHz $^1$H NMR. The chemical shifts of the anomeric- and methyl-protons in the sugar chains c, e and f attached to laccase are also shown in Table 4:

TABLE 4

| | Chemical shift of anomeric proton (δppm, D$_2$O) | | | | | | | | | | |
|---|---|---|---|---|---|---|---|---|---|---|---|
| Sugar chain | GlcNAc-2 | Man-3 | Man-4 | Man-4' | GlcNAc-5 | GlcNAc-5' | Gal-6 | Gal-6' | Fuc-1 | Fuc-2 | Xyl |
| c | 4.592 | 4.857 | 5.140 | 4.899 | 4.511 | 4.536 | — | — | 5.048 | — | 4.425 |
| A | 4.596 | 4.849 | 5.139 | 4.897 | 4.512 | 4.544 | — | — | 5.042 | — | 4.427 |
| B | 4.630 | 4.860 | 5.137 | 4.898 | 4.513 | 4.579 | — | 4.503 | — | 5.005 | 4.415 |
| e | 4.591 | 4.855 | 5.139 | 4.900 | 4.511 | 4.576 | — | 4.499 | 5.047 | 5.000 | 4.424 |
| C | 4.592 | 4.849 | 5.139 | 4.901 | 4.514 | 4.578 | — | 4.499 | 5.042 | 5.001 | 4.427 |
| f | 4.592 | 4.856 | 5.139 | 4.901 | 4.533 | 4.576 | 4.490 | 4.499 | 5.048 | 4.499 | 4.423 |
| D | 4.593 | 4.853 | 5.139 | 4.900 | 4.534 | 4.578 | 4.491 | 4.498 | 5.045 | 5.001 | 4.424 |

| | Chemical shift of methyl proton (δppm, D$_2$O) | | | | |
|---|---|---|---|---|---|
| Sugar chain | GlcNAc-2 | GlcNAc-5 | GlcNAc-5' | Fuc-1 | Fuc-2 |
| c | 2.043 | 2.043 | 2.043 | 1.197 | — |
| A | 2.044 | 2.044 | 2.044 | 1.192 | — |
| B | 2.041 | 2.041 | 2.041 | — | —* |
| e | 2.042 | 2.042 | 2.042 | 1.195 | 1.170 |

TABLE 4-continued

| | | | | | |
|---|---|---|---|---|---|
| C | 2.043 | 2.043 | 2.043 | 1.191 | 1.171 |
| f | 2.042 | 2.042 | 2.042 | 1.197 | 1.170 |
| D | 2.041 | 2.041 | 2.041 | 1.195 | 1.170 |

Note:
Chemical shifts were measured with internal acetone ($\delta = 2.216$ ppm) at 30° C. In the table, the symbol "Fuc-1" represents fucose residue which couples to GlcNAc-l; the symbol "Fuc-2" represents fucose residue which couples to GlcNAc-2 or GlcNAc-5', and the symbols "Gal-6" and "Gal-6'" represent galactose residue which couples to GlcNAc-5 or GlcNAc-5'. The symbol "—*" represents that no signal was detectable due to the limited amount of the sample.

As shown in Table 4, the sugar chains c, e and f, which were reported by N. TAKAHASHI et al., and shown by the following chemical formulae 2, 3, and 4, have N-linked sugar-chain structures consisting of 4 N-acetylglucosamine residues and 3 mannose residues having side chains of Fucα1, Xylβ1 and/or Galβ1. Based on these findings, the sugar chains A to D are respectively estimated to have the following structures as shown by the chemical formulae 5, 6, 7 and 8, and, therefore, the sugar chains which are attached to the present protein can be represented by the chemical formula 2. Now briefly supplementing the nuclear magnetic resonance spectrum of the sugar chain B, no signal of anomeric- and methyl-protons corresponding to that of Fuc-1 residue in Table 4 was detectable, and the chemical-shift value of GlcNAc-2 was shifted to a low magnetic field of 4.630 ppm which is lower than 4.591 ppm as in the sugar chain e. The results indicated that the sugar chain B has a structure of the sugar chain e wherein Fucα1 is lacking.

Chemical formula 2:
(Sugar chain of laccase c)

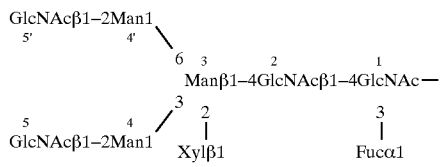

Chemical formula 3:
(Sugar chain of laccase e)

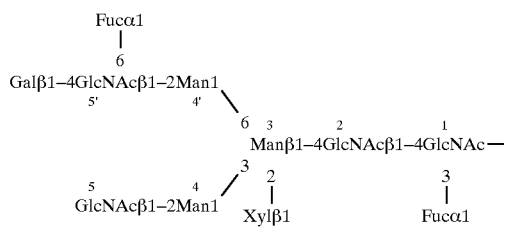

Chemical formula 4:
(Sugar chain of laccase f)

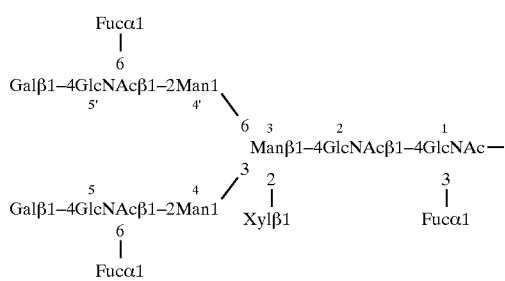

Chemical formula 5:
(Sugar chain A)

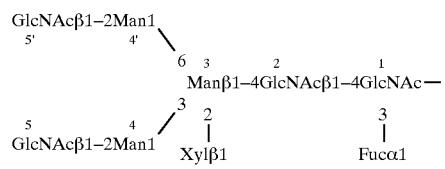

Chemical formula 6:
(Sugar chain B)

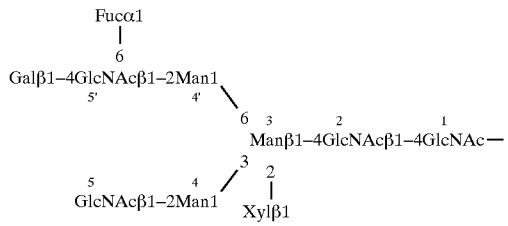

Chemical formula 7:
(Sugar chain C)

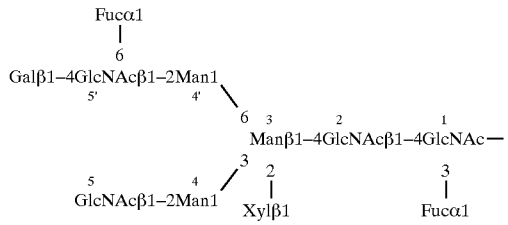

Chemical formula 8:
(Sugar chain D)

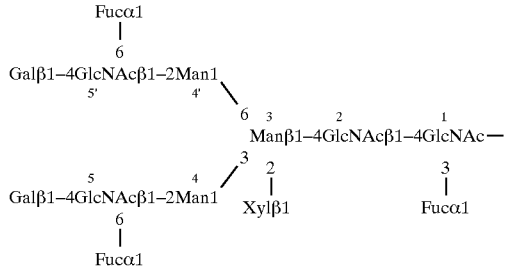

EXPERIMENT 2-5

Ultraviolet absorption spectrum

The purified protein obtained in Experiment 1 exhibited the maximum ultraviolet absorption spectrum at a wave length around 280 nm when measured with a spectrophotometer in an aqueous solution.

EXPERIMENT 2-6
Solubility in solvent

The purified protein obtained in Experiment 1 was soluble in water, physiological saline and phosphate buffer when tested in the usual manner.

EXPERIMENT 2-7
Biological activity

The purified protein obtained in Experiment 1 induces the growth of T-cells which specifically react with the protein, and couples to an immunoglobulin E antibody prepared from a patient with pollenosis when tested by the following experiments. The sugar chain attached to the present protein has a specific immunological property, and the removal thereof from the protein results in a significant reduction of the antigenicity of the protein.

EXPERIMENT 2-7(a)
Test on T-cell growth induction

By using ficoll-hypaque gradient centrifugation, mononuclear cells were isolated from heparinized peripheral blood which had been collected from a patient with pollenosis. The mononuclear cells were suspended in RPMI 1640 medium (pH 7.0) supplemented with 10 v/v % AB serum to give a cell density of $1\times10^6$ cells/ml, admixed with 20 $\mu$g/ml of the purified protein in Experiment 1, and incubated in an incubator at 37° C. for 5 days in 5 v/v % $CO_2$ atmospheric conditions. Thereafter, 50 units/ml of a recombinant human interleukin 2 was added to the resultant culture which was then further incubated similarly as above for 9 days. The resultant cells, pretreated in this manner, were used in the following T-cell growth test.

To a 96-well microplate were added $4\times10^4$ cells/well of the mononuclear cells suspended in RPMI 1640 medium (pH 7.0) supplemented with 10 v/v % AB serum, $1\times10^6$ cells/well of peripheral mononuclear cells which had been collected from the same patient and incubated at 37° C. for 30 min in the presence of 50 $\mu$g/ml mitomycin C, 50 $\mu$g/ml of the purified protein in Experiment 1, and a fresh preparation of the same medium as used above to give a total volume of 200 $\mu$l/well. The cells were successively incubated under 5 v/v % $CO_2$ atmospheric conditions at 37° C. for 2 days, admixed with 0.5 $\mu$Ci/well $^3$H-thymidine, and incubated for one day, followed by counting the uptake amount of $^3$H-thymidine on a scintillation counter. In parallel, a system using a medium free of the present protein was arranged as control and treated similarly as above. As a result, the control system showed about 200 cpm uptake of $^3$H-thymidine, while the system with the protein showed about 8,500 cpm uptake of $^3$H-thymidine per 50 $\mu$g/ml of the purified protein, and this revealed that the purified protein might strongly accelerate the T-cell growth in pollenosis patients' blood. This also means that the protein has an antigenicity.

EXPERIMENT 2-7(b)
Test on conjugation with immunoglobulin E antibody

Two hundred and fifty $\mu$g of the purified protein in Experiment 1 was dissolved in a small amount of distilled water, and the resultant solution was dialyzed against distilled water for 18 hours. The dialyzed solution was lyophilized, dissolved in 125 $\mu$l of 2M acetate buffer (pH 7.8) containing 0.5 w/v % sodium dodecyl sulfate (SDS) and 50 mM 2-mercaptoethanol, and heated at about 100° C. for 10 min. The resultant solution was admixed with 60 $\mu$l of 7.5 w/v % Nonidet P-40, a nonionic detergent, 5 units of N-glycanase, 200 $\mu$l of distilled water, and incubated at 37° C. for 24 hours to release sugar chains from the protein. As a control, a system, wherein N-glycanase was not used, was prepared and treated similarly as in the above.

To 96-well microplate was adsorbed the purified protein of Experiment 1 in an amount of one $\mu$g/well, and a serum preparation prepared from a healthy volunteer or a patient with pollenosis was added to the wells in an amount of 100 $\mu$l/well, followed by incubating the microplate at 37° C. for 2 hours. The microplate was washed with 0.1M phosphate buffer (pH 7.2) containing 0.1 v/v % calf serum albumin to remove non-adsorbed serum, and an anti-human immunoglobulin E antibody, prepared from a goat and labelled with peroxidase from horseradish, was added to the wells of the microplate in an amount of 100 $\mu$l/well, followed by further incubating the microplate at 37° C. for 2 hours. Thereafter, the microplate was washed with a fresh preparation of the same phosphate buffer used above to remove non-adsorbed antibody, and to each well of which was added 100 $\mu$l of 0.1M citrate buffer (pH 5.0) containing 0.5 mg/l of o-phenylenediamine and 0.03 v/v % hydrogen peroxidase to effect coloration, followed by measuring the absorbance of a solution in each well at 492 nm.

As a result, the absorbance in the system using the protein free of sugar chain was about 0.05, while that in the system using the protein with sugar chain(s) was as high as about 0.3, and this indicates that the present protein specifically conjugates with immunoglobulin E antibodies contained in the blood of patients with pollenosis, and that the sugar chains are required to exhibit the antigenicity of the protein. Furthermore, the results in Experiment 2-7 confirm the fact that the present protein is a substance which causes pollenosis, i.e., it has a property to induce pollenosis in mammals including human.

EXPERIMENT 2-8
Stability

No residual activity was detected when the purified protein in Experiment 1 was incubated in an aqueous solution (pH 7.2) at 100° C. for 10 min. No substantial loss of activity was observed even after a 1-month incubation of the purified protein in an aqueous solution (pH 7.2) at 4° C.

Any protein having these properties has not yet been known, and one can thus conclude that the present protein is a novel substance.

Now explaining the process to produce the present protein, it can be prepared by collecting pollen from cedar such as "omote-sugi" or "ura-sugi", i.e. *Cryptomeria japonica*, extracting the pollen with an aqueous solvent and purifying the extract. The methods to extract the present protein from cedar pollens used in the invention are generally those which comprise collecting pollen from male flowers of cedar; suspending the pollen in water or an aqueous solvent such as those of a readily water-soluble organic solvent of methyl alcohol, ethyl alcohol, acetone or the like, or in an aqueous solvent admixed with an adequate amount of a stabilizer or the like; and soaking the pollen while stirring if required in such a solvent at a temperature lower than 10° C., preferably, about 0°–5° C., for 30 min or longer, preferably, about 1–2 hours. Depending on the conditions of the cedar pollen used, the aforesaid procedure is usually carried out 1 to 5 times to extract the most of the protein from the material cedar pollen.

The protein in the resultant extract can be purified by conventional techniques in general used in this field. Partially-purified protein can be obtained from the extract by using a method such as salting out, dialysis, filtration, centrifugation, gel filtration chromatography, etc. Such a partially-purified protein generally contains cedar pollen allergens such as *Cry j* II together with the present protein.

In case a more highly-purified protein is required, it is obtainable by removing components such as *Cry j* II and contaminants other than the present protein with one or more methods such as gel filtration chromatography, ion-exchange chromatography, affinity chromatography, electrophoresis, isoelectrophoresis, etc.

The partially purified- and highly purified-proteins thus obtained can be arbitrarily incorporated into or used as desensitization agents for diagnosing, treating and/or preventing pollenosis. The purified protein is useful as an antigen for detecting immunoglobulin E antibodies, which have a specificity to the protein, for qualitative and quantitative analyses by enzyme immunoassay and radioimmunoassay, and extensively applicable in the diagnosis of pollenosis and the scientific study to reveal the induction mechanisms of allergies in general.

The following examples concretely explain the process for producing the present protein:

EXAMPLE A-1

Preparation of partially-purified protein

One part by weight of a cedar pollen prepared from male flowers of "omote-sugi", i.e. *Cryptomeria japonica*, grown in Chiba, Japan, was suspended in about 16 parts by weight of an aqueous solution of 0.125M sodium hydrogen carbonate (pH 8.2) to effect extraction while stirring at 4° C. for one hour, followed by centrifuging the resultant extract to obtain a supernatant. The sediment was treated similarly as above to obtain a supernatant which was then pooled with the above supernatant. To the mixture was added 0.1 w/v % "CETAVLON", hexadecyltrimethylammonium bromide commercialized by Sigma, Chemicals Co., St. Louis, USA, and the mixture was centrifuged to obtain a supernatant which was then mixed with ammonium sulfate to give a saturation degree of 80 w/w % to salt out proteinaceous components. The resultant sediment was dialyzed against 50 mM Tris-HCl buffer (pH 7.8) for 10 hours, and the dialyzed solution was filtered to obtain a filtrate which was then fed to a column packed with DEAE-SEPHADEX® which had been previously equilibrated with 50 mM Tris-HCl buffer (pH 7.8), followed by recovering non-adsorbed fractions. The non-adsorbed fractions were pooled, adjusted to pH 5.0 by the addition of acetic acid, and fed to a column packed with "CM-SEPHADEX" which had been previously equilibrated with 10 mM acetate buffer (pH 5.0). The column was washed by feeding thereto 10 mM acetate buffer (pH 5.0), and fed with an eluant consisting of 0.1M phosphate buffer (pH 7.0) and 0.3M sodium chloride to elute the proteinaceous components. Thereafter, the resultant eluate was concentrated and lyophilized to obtain a partially-purified protein containing *Cry j* II along with the present protein. The yield was about 0.1% against the weight of the material cedar pollen, d.s.b.

The partially purified protein thus obtained can be suitably used as desensitization agent for diagnosing, treating and/or preventing pollenosis.

EXAMPLE A-2

Purified protein

A partially-purified protein obtained by the method in Example A-1 was dissolved in a small amount of distilled water, and the solution was fed to a column packed with "MONO-S" which had been previously equilibrated with 10 mM phosphate buffer (pH 5.0). The column was fed with a liner gradient buffer of salt increasing from 0M to 0.5M in 10 mM Tris-HCl buffer (pH 7.0), followed by the elution of the present protein at a salt concentration of 0.1M to 0.3M. Thereafter, the eluate was concentrated and lyophilized to obtain a purified protein substantially consisting of the present protein. The yield was about 0.02% against the weight of the material cedar pollen, d.s.b.

The purified protein can be suitably used as a desensitization agent for diagnosing, treating and/or preventing pollenosis, as well as being used as an antigen for enzyme immunoassay and radioimmunoassay.

The uses of the present protein will be explained with reference to the following examples and experiments.

Since the present protein is one of the major substances causative of pollenosis, it can be extensively used as a desensitization agent for diagnosing, treating and/or preventing pollenosis. The desensitization agent according to the present invention comprises as an effective ingredient the present protein or the later described conjugate of the protein and a specific saccharide. As regards a desensitization agent directed to diagnosis of pollenosis, it can be generally prepared by mixing with a carrier a partially purified- or a highly purified-protein prepared by the aforesaid methods. As regards a desensitization agent directed to the treatment and/or prevention of pollenosis, it can be prepared into a conjugate prior to the mixing as mentioned above by allowing the present protein to couple with a specific saccharide.

The specific saccharides as referred to in the invention include those which can covalently couple to the present protein to form conjugates whereby the desensitization efficacy of the protein is significantly augmented and/or the side effects are significantly reduced. Examples of such a saccharide are homo or heteropolysaccharides such as starch, amylose, dextran, polysucrose, pullulan, elsinan, curdlan, gum arabic, gum tragacanth, guar gum, xanthan gum, carrageenan, cellulose, glucomannan, chitosan, lipopolysaccharides, and their derivatives and partial hydrolysates. Usually, the average molecular weight of such a saccharide is in the range of about 500–10,000,000 daltons, preferably, about 10,000–1,000,000 daltons. Among these saccharides, pullulan and elsinan, which substantially consist of repeating maltotriose units, as well as their partial hydrolysates, are prepared with the protein into conjugates which induce immunoglobulin G and M antibodies which are effective for desensitization by a large margin when administered to mammals including human, but do not substantially form immunoglobulin E antibody, a major factor causative of unsatisfactory side effects including anaphylactic shock. These properties are advantageously useful in the desensitization therapy which requires a repeated administration of medicaments in order to attain a considerably-high effect without a fear of causing unsatisfactory side effects.

For example, lipopolysaccharides derived from microorganisms of *Escherichia coli*, Salmonella, Serratia, etc. and their partial hydrolysates exert the following features when prepared with the present protein into conjugates: Such a lipopolysaccharide increases the affinity of the protein for the mucosae of mammals and significantly improves the intake efficiency of the protein. For this reason, conjugates of the present protein and the saccharides are advantageously useful as desensitization agents which are used for percutaneous and/or permucosal administration.

Usually, such a conjugate can be prepared by reacting the present protein with an activated saccharide or by bridging the protein with a saccharide by using a reagent having one or more active functional groups. Examples of such a reaction are the diazo method, peptide method, alkylation method, bridging method, amide binding method, peroxidase oxidation method, disulfide binding method, etc., and these methods themselves are known in this art. A representative of such a method is described in detail, for example, in Japanese Patent Laid-Open No.93,730/91. The ratio of the protein to a saccharide at the initiation of the reaction suitably used in the invention is usually in the range of about 1:0.001 to 1:1,000, preferably, about 1:0.01 to 1:100, d.s.b. Depending on the reaction methods used, molecules of the protein readily couple to each other when the ratio is below the range, while molecules of the saccharide readily react with each other when the ratio exceeds the range. Anyway, any ratios other than those specified in the invention result in reductions of reactivity and purification efficiency of the reaction products, and this indicates that the above-specified ratios are the best mode. The reaction temperature, pH and time used in the present invention are chosen so as not to inactivate or decompose the protein or to reduce the side reactions as much as possible, and, usually, a temperature of about 0°–100° C. and a pH of about 0.1–12 are suitably used to complete the reaction within about 0.1–50 hours.

The conjugates obtained by the above reaction can be purified by conventional methods such as dialysis, salting out, filtration, concentration, centrifugation, gel filtration chromatography, ion-exchange chromatography, affinity chromatography, electrophoresis, isoelectrophoresis, etc., and, if necessary, such a conjugate can be purified by an appropriate combination of the above methods. The resultant purified conjugates may be concentrated and lyophilized into liquid or solid products for final use.

The desensitization agent according to the present invention includes the aforesaid protein and/or conjugates, and other compositions comprising either of the protein or a conjugate along with a physiologically acceptable carrier, excipient, diluent, adjuvant and/or stabilizer, and one or more medicaments, for example, an antihistamine and an anti-inflammatory agent such as a steroid hormone or disodium cromoglycate. The desensitization agent may be in a dose form, i.e. those which contain the present protein or conjugate in an amount suitable for a dose per day or in an amount up to 4 times by integers or up to ¹⁄₄₀ times of the dose, and may be a physically separated form suitable for a prescribed administration. Examples of the form of such a pharmaceutical agent are a powder, parvule, granule, pearl, tablet, capsule, troche, syrup, emulsion, ointment, emplastrum, pap, suppository, collyrium, collunarium, nebula, injection, etc.

Now explaining the use of the present desensitization agent, it can be used similarly as conventional desensitization agents which contain cedar pollen allergens. For using the present desensitization agent for diagnosing pollenosis, patients are scratched on their skin surfaces with a care not to draw blood using conventional tests known as the scratch or intradermal-test, and an adequate amount of the present desensitization agent for diagnosis was dropped onto the scratched sites. Alternatively, patients are intradermally injected with an adequate amount of the desensitization agent. Thereafter, the occurrence and the size of urtica formed 15–30 min after the dropping or injecting are examined and measured, and a positive reaction obtained when the size of the urtica exceeded a prescribed level.

In the treatment using the present desensitization agent, an appropriate dose and application thereof are usually determined based on the results of the aforesaid diagnosis. Patients with a positive result in the diagnosis are treated orally or parenterally with the present desensitization agent containing a conjugate of the present protein and a specific saccharide. Depending on the symptoms and/or administration routes, patients are usually treated repeatedly via the route of an intradermal, subcutaneous, intramuscular, intraperitoneal or permucosal administration with the present desensitization agent at a dose of about 0.0001–100,000 ng/shot/adult, preferably, a dose of about 0.001–10,000 ng/shot/adult and a frequency of one shot per week or month for about 1–12 months while usually increasing the dose. In case of using the present desensitization agent in the prevention of pollenosis, approximately the same dose and application as used in the treatment of pollenosis can be used, and patients are usually treated repeatedly with the desensitization agent at a dose of about 0.0001–100,000 ng/shot/adult, preferably, a dose of abut 0.001–10,000 ng/shot/adult, and a frequency of one shot per week or month for about 1–6 months while usually increasing the dose via the route of an intradermal, subcutaneous, intramuscular or permucosal administration while observing the patients' conditions and symptoms. When the present desensitization agent is repeatedly administered to patients in a prescribed time interval from the beginning of autumn to the following early spring, predictable allergic symptoms of the patients which might be induced in the forthcoming season would be substantially reduced or completely avoided.

The desensitization agent according to the present invention will be described concretely with reference to the following several examples:

EXAMPLE B-1

Dried injection

Two g of a purified pullulan having an average molecular weight of about 200,000 daltons was dissolved in 100 ml distilled water, and the solution was mixed with 2 ml of 1.7 w/v % cyanuric chloride in acetone solution. Thereafter, the resultant mixture was reacted by allowing it to stand at 4° C. or lower for 2 hours in an ice-chilled water bath while the pH was controlled to around 7 by the addition of 5 w/v % aqueous sodium carbonate solution. The resultant solution containing an activated pullulan was mixed with 40 mg of a purified protein obtained by the method in Example A-2, and allowed to react at 37° C. and pH 7.0 for 5 hours under stirring conditions. After completion of the reaction the resultant was mixed with one w/v % glycine and incubated at 37° C. for 2 hours while stirring to block the intact activated groups, and the resultant mixture was dialyzed against 0.01M acetate buffer (pH 5.0) for 5 hours, fed to a column packed with "CM-SEPHADEX" which had been previously equilibrated with 0.01M acetate buffer (pH 5.0), followed by recovering the resultant conjugate of the protein and pullulan from non-adsorbed fractions. The conjugate was in the usual manner dissolved in physiological saline supplemented with one w/v % human serum albumin to give a final concentration of about 100 ng/ml, and the solution was membrane filtered, distributed to sterile vials by 2 ml aliquots, lyophilized and cap sealed.

In use, one ml distilled water for injection is added to each vial, and the contents are dissolved to homogeneity prior to administration. The product, which contains the conjugate of the protein and pullulan as an effective ingredient, can be arbitrarily useful as dried injection for treating and/or preventing pollenosis.

EXAMPLE B-2

Injection

One g of CM-cellulose having an average molecular weight of about 20,000 daltons was dissolved in 200 ml distilled water, and the solution was mixed with 2 g 1-ethyl-3-(3-dimethyl-aminopropyl)carbodiimide-methiozide, followed by reacting the resultant solution at ambient temperature for 2 hours while stirring and keeping at a pH of around 4 by the addition of 1N hydrochloride. The reaction mixture was dialyzed against distilled water for 24 hours, and the dialyzed solution was recovered, mixed with 30 mg of a purified protein obtained by the method in Example A-2, and allowed to stand to react the contents at ambient temperature and pH 4.5 for 15 hours. Thereafter, the resultant conjugate in the reaction mixture was purified similarly as in Example B-1, concentrated, dissolved in 50 v/v % aqueous glycerine solution, membrane filtered, distributed to sterile vials by 2 ml aliquots, and cap sealed.

With reference to the diagnostic results of the scratch- or intradermal-test, the product is admixed with 100-fold to 100,000-fold volumes of 50 v/v % aqueous glycerine solution to dilute the contents to homogeneity prior to administration. The product containing the conjugate of the present protein and CM-cellulose can be arbitrarily used as a desensitization agent for treating and/or preventing pollenosis.

EXAMPLE B-3
Liquid preparation

One hundred mg of a purified lipopolysaccharide derived from a microorganism of the genus Salmonella was dissolved in 25 ml of an about 4° C. aqueous solution of sodium acetate with a degree of saturation of 50 w/v %, and the resultant solution was adjusted to pH 9.0 by the addition of 0.5N sodium hydroxide, followed by adding thereto drop by drop one ml anhydrous dioxane containing 20 µl bromoacetyl bromide while keeping at a pH around 8.5. Thereafter, the resultant solution was adjusted to a pH of about 4.5 by the addition of 6N acetic acid, dialyzed against 4° C. distilled water for 48 hours to obtain an aqueous solution containing an activated lipopolysaccharide. To the aqueous solution was added 40 mg of a purified protein obtained by the method in Example A-1, followed by allowing the mixture to react at ambient temperature for 48 hours while keeping at a pH of about 4.5. Thereafter, the reaction mixture was purified similarly as in Example B-1, concentrated, lyophilized to obtain a solid conjugate of the present protein and lipopolysaccharide. The solid conjugate was dissolved in distilled water containing one w/v % purified gelatin to give a final concentration of 100 ng/ml, and the resultant solution was in a usual manner membrane filtered to obtain a liquid preparation.

The product, containing a conjugate of the present protein and lipopolysaccharide, can be arbitrarily used as liquid preparation for a collyrium, collunarium or nebula for oral cavity to treat and/or prevent pollenosis.

EXAMPLE B-4
Sublingual tablet

A purified elsinan having an average molecular weight of about 200,000 daltons was dissolved to homogeneity in 400 ml distilled water, and the solution was adjusted to pH 10.7 by the addition of 1N sodium hydroxide, gradually admixed with 3 g cyanogen bromide while keeping at a pH around 10.0, and reacted for one hour. The reaction mixture was adjusted to pH 5.0 by the addition of 1N hydrochloride, and dialyzed against cold water for 10 hours while maintaining the pH, followed by recovering an aqueous solution containing an activated elsinan. To the aqueous solution was added 20 mg of a purified protein obtained by the method of Example A-2, and the resultant was allowed to stand at ambient temperature for 24 hours to react the contents. After completion of the reaction, the reaction mixture was mixed with 3-fold volumes of acetone, followed by recovering the formed precipitate, dissolving it in 0.01M acetate buffer (pH 5.0), and removing insoluble substances by centrifugation. The supernatant thus obtained was fed to a column packed with "CM-SEPHADEX" which had been previously equilibrated with 0.01M acetate buffer (pH 5.0), followed by recovering fractions containing a conjugate of the present protein and elsinan. The fractions were in usual manner pooled, membrane filtered, concentrated, pulverized and mixed to homogeneity with "FINETOSE®", an anhydrous crystalline α-maltose powder commercialized by Hayashibara Co., Ltd., Okayama, Japan. The resultant mixture was in a usual manner tabletted with a tabletting machine to obtain tablets, 200 mg weight each, containing 100 ng of the present protein per tablet.

The product, having a satisfactory stability and applicability, can be arbitrarily used as sublingual agent for treating and/or preventing pollenosis. EXAMPLE B-5
Diagnostic agent Ten mg of a partially-purified protein obtained by the method of Example A-1 was dissolved in 20 ml of physiological saline, and the solution was in a usual manner membrane filtered, distributed to sterile vials by one ml aliquots, lyophilized and cap sealed.

The product is dissolved in one ml of distilled water for injection, diluted by 10 fold with a fresh preparation of the same distilled water prior to use, and used in the diagnosis of pollenosis by the scratch- and intradermal-tests.

EXAMPLE B-6
Diagnostic agent

One mg of a purified protein obtained by the method in Example A-2 was dissolved in 20 ml of 50 v/v % glycerine containing 5 w/v % sodium chloride, and the resultant solution was in a usual manner membrane filtered and distributed to sterile vials by one ml aliquots.

The product is diluted by 20-fold with a 50 v/v % aqueous glycerine solution and used in the diagnosis of pollenosis by the scratch- and intradermal-tests.

The following several experiments explain the efficacy of the present desensitization agent:

EXPERIMENT 3
Animal experiment

This experiment was carried out to demonstrate that the present conjugate of the protein and a specific saccharide according to the invention is effective for the treatment and/or prevention of pollenosis when administered to experimental animals.

EXPERIMENT 3-1
Prophylactic effect

Six female BALB/c mice, 10–12-week-old, in a group, were intraperitoneally injected with a desensitization agent obtained by the method at Example B-1 in a dose of one µg/mouse of the protein per week over 3 weeks. One week after the final injection, pollenosis was induced in the mice by injecting them similarly as above with 0.2 ml of a physiological saline, containing 4 mg aluminum hydroxide as adjuvant and one µg of a purified protein obtained by the method in Example A-2 as antigen. The blood of the mice was sampled immediately before and one week after the administration of the antigen, and the blood samples were examined for the amounts of immunoglobulin G and M antibodies specific to the protein.

As a control system, mice were treated with a mixture containing a purified protein, obtained by the method of Example A-2, and a purified pullulan having an average molecular weight of about 200,000 daltons in a weight ratio of 1:15, and treated similarly as above. The amount of immunoglobulin E antibody which is specific to the present protein was assayed by the passive cutaneous anaphylaxis (PCA) reaction as reported by I. Mota and D. Wong in *Life Sciences*, Vol.8, No.16, Part II, pp.813–820 (1969), and the amount of immunoglobulin M antibody which is specific to the present protein was assayed by the enzyme immunoassay as reported by S. YOSHITAKE in *The Journal of Biochemistry*, Vol.92, No.5, pp.1,413–1,424 (1982). The amount of each antibody was expressed with an average value of antibody titers of 6 mice. The results were as shown in Table 5:

TABLE 5

| Desensitization agent | Immediately before administration | | One week after administration | | Judgement |
|---|---|---|---|---|---|
| | IgG + IgM | IgE | IgG + IgM | IgE | |
| Conjugate of protein and pullulan | 235 | 0 | 970 | 3 | Present invention |
| Mixture of protein and pullulan | 30 | 15 | 245 | 320 | Control |

Note:
In the table, "protein" means the present protein; "IgG", immunoglobulin G; "IgM", immunoglobulin M; and "IgE", immunoglobulin E.

As is evident from the results in Table 5, compared with the control system, the system, wherein the mice had been previously treated with the desensitization agent containing the conjugate of the present protein and pullulan, showed a relatively-high productivity of immunoglobulin G and M antibodies which are effective for desensitization, while the formation of immunoglobulin E antibody in the mice was substantially inhibited. The inhibitory activity of forming immunoglobulin E antibody, exerted by the present desensitization agent administered to mice, indicates that the agent can be safely and effectively used in the prevention of pollenosis of mammals including human with the viewpoint of that immunoglobulin E antibody is known as a major factor which causes unsatisfactory side effects including anaphylactic shock.

EXPERIMENT 3-2
Therapeutic effect by parenteral administration

Pollenosis was induced in 6 female BALB/c mice, 10–12-weeks old, in a group, by intraperitoneally injecting them once a week over 3 weeks with 0. 2 ml of a physiological saline containing one µg of a purified protein as antigen, obtained by the method of Example A-2, and 4 mg aluminum hydroxide as adjuvant. One week after the final administration of the antigen, the mice were injected once a week over 3 weeks similarly as above with a desensitization agent obtained by the method of Example B-1 at a dose of 100 ng/mouse of the protein, d.s.b. One week after the final administration of the desensitization agent, the mice were further administered only the antigen to reinduce immunoglobulin E antibody. The blood of the mice was sampled immediately before the administration of the desensitization agent, one week after the final administration of the desensitization agent, and one week after the reinduction of immunoglobulin E antibody, and the blood samples were assayed by the same method as in Experiment 3–1 for determining the amounts of immunoglobulin E, G and M antibodies which are specific to the protein.

As a control system, mice were administered a mixture, containing a purified protein, obtained by the method of Example A-2, and a purified pullulan having an average molecular weight of about 200,000 daltons in a weight ratio of 1:15 in place of the desensitization agent as used above, and treated similarly as above. The results were as shown in Table 6:

TABLE 6

| Desensitization agent | Immediately before administration | | One week after administration | | One week after reinduction of IgE | | Judgement |
|---|---|---|---|---|---|---|---|
| | IgG + IgM | IgE | IgG + IgM | IgE | IgG + IgM | IgE | |
| Conjugate of protein and pullulan | 350 | 185 | 2,550 | 35 | 5,800 | 45 | Present invention |
| Mixture of protein and pullulan | 340 | 180 | 475 | 370 | 2,400 | 1,300 | Control |

Note:
In the table, "protein" means the present protein; "IgG", immunoglobulin G; "IgM", immunoglobulin M; and "IgE", immunoglobulin E.

As is evident from the results in Table 6, compared with the control system, the system in which the mice were administered the present desensitization agent containing a conjugate of the present protein and pullulan resulted in the formation of relatively-large amounts of immunoglobulin G and M antibodies both after the administration of the desensitization agent and the reinduction of immunoglobulin E antibody. As regards immunoglobulin E antibody, the formation was substantially inhibited even before the administration of the desensitization agent and after the reinduction of immunoglobulin E antibody. These results confirm that pollenosis of mammals including humans could be safely and effectively treated by the parenteral administration of the present desensitization agent containing the conjugate.

EXPERIMENT 3-3
Therapeutic effect by oral administration

Pollenosis was induced in 6 female BALB/c mice, 10–12-weeks old, in a group, by intraperitoneally injecting them once a week over 3 weeks with 0.2 ml of a physiological saline containing one µg of a purified protein as antigen, obtained by the method of Example A-2, and 4 mg aluminum hydroxide as adjuvant. One week after the final administration of the antigen, the mice were administered orally once a week over 3 weeks similarly as above a sublingual agent, obtained by the method in Example B-4, at a dose of 100 ng/mouse of the protein, d.s.b. One week after the final administration of the sublingual agent, the blood of the mice was sampled, and the blood samples were assayed for the amounts of immunoglobulin A, G and E antibodies which are specific to the protein.

As a control system, mice were administered orally a solid mixture containing a purified protein, obtained by the method of Example A-2, and a purified lipopolysaccharide derived from Salmonella in a weight ratio of 1:15, and treated similarly as above. The amounts of immunoglobulin A and G antibodies, which are specific to the present protein, were assayed by the enzyme immunoassay (EIA) as reported by R. Maiolini et al. in *Journal of Immunological Methods*, Vol.6, pp.355–362 (1975), and the amount of immunoglobulin E antibody was assayed with the same method as in Experiment 3-1. The amounts of immunoglobulin A, G and E antibodies were respectively expressed with an average value of antibody titers of 6 mice. The results were as shown in Table 7:

TABLE 7

| Desensitization agent | Immediately before administration | | One week after administration | | Judgement |
| --- | --- | --- | --- | --- | --- |
| | IgA + IgG | IgE | IgA + IgG | IgE | |
| Conjugate of protein and lipopolysaccharide | 330 | 165 | 2,250 | 25 | Present invention |
| Mixture of protein and lipopolysaccharide | 325 | 185 | 410 | 310 | Control |

Note:
In the table, "protein" means the present protein; "IgA", immunoglobulin A; "IgG", immunoglobulin G; and "IgE", immunoglobulin E.

As is evident from the results in Table 7, compared with the control system, the system, wherein the mice were administered with the desensitization agent containing the conjugate of the present protein and lipopolysaccharide, showed a relatively-large productivity of immunoglobulin A and G antibodies, while the production of immunoglobulin E was substantially inhibited. These results confirm that the present desensitization agent containing the conjugate can safely and effectively treat pollenosis of mammals including humans even when administered orally.

Although the data are not shown, significant therapeutic and/or prophylactic effects were exerted on pollenosis without a fear of causing unsatisfactory side effects even when the protein was administered to mice, rats and guinea pigs were intradermally, subcutaneously, intramuscularly or intraperitoneally by conventional methods as used in this field with a desensitization agent obtained by the methods in Examples B-1 to B-4, or permucocutaneously administered with such a desensitization agent in the form of a collyrium, collunarium or nebula for oral cavity. It was revealed that such an effect was more augmented when a conjugate of the present protein and a saccharide which consists essentially of repeating maltotriose units such as pullulan and elsinan was used, and, in this case, the dose and administration period required for attaining the objective desensitization effect were more reduced or shortened as compared with other conjugates prepared by using saccharides other than pullulan and elsinan.

EXPERIMENT 3-4

Acute toxicity test

By using a conventional method, mice, 20-day-old, were orally or intraperitoneally treated with therapeutic and/or prophylactic desensitization agents obtained by the method of Examples B-1 to B-4. As a result, it was revealed that the $LD_{50}$ of the desensitization agents was 1,000,000 ng or more by any administration route. The results confirm that the present desensitization agent containing the present protein and a specific saccharide can be used in pharmaceuticals for administering to mammals including humans without fear of causing side effects.

As is described above, the protein according to the present invention is a novel substance which causes pollenosis. The protein induces pollenosis in mammals including humans, and because of this it is widely applicable to use as desensitization agents for diagnosing, treating and/or preventing pollenosis, as well as to diagnosis of pollenosis using enzyme immunoassay and radioimmunoassay, and to researches for elucidating the mechanisms of allergy induction in general. More particularly, the conjugates of the protein and a specific saccharide according to the present invention induce the production of immunoglobulin antibodies which are effective to desensitization when administered to mammals including humans, and do not substantially form immunoglobulin E antibody which is a major factor causative of unsatisfactory side effects such as anaphylactic shock. Because of these properties, the present desensitization agent effectively reduces the dose of an antigen and even shortens the administration period required for the treatment and/or prevention of pollenosis. The protein with these useful properties can be readily prepared from cedar pollens as starting material in a satisfactory-high yield by the present process.

The present invention exerts the aforesaid outstanding effects and has a great significance and contribution to the field.

While there have been described what are at present considered to be the preferred embodiments of the invention, it will be understood the various modifications may be made therein, and it is intended to cover in the appended claims all such modifications as fall within the true spirit and scope of the invention.

We claim:

1. A desensitization agent for treating and/or preventing pollenosis comprising a pharmaceutically acceptable carrier and a mixture of proteins selected from proteins having the following physicochemical properties as effective ingredients:

(1) Molecular weight
Exhibiting a band in a position corresponding to 44,000 to 54,000 daltons on sodium dodecyl sulfate polyacrylamide gel electrophoresis (SDS-PAGE);

(2) Isoelectric point (pI)
Exhibiting isoelectric points corresponding to 8.5 to 9.2 on isoelectrophoresis;

(3) Partial amino acid sequence containing the C-terminal Asn-Gly-Asn-Ala-Thr-Pro-Gln-Leu-Thr-Lys-Asn-Ala-Gly-Val-Leu-Thr-Cys-Ser-Leu-Ser-Lys-Arg-Cys (SEQ ID NO:3);

(4) Sugar content
Containing sugar chains having chemical structures in the molecule as shown by the following chemical formulae; where "X", "X'" and "X''" represent a hydroxyl group or Fucα1, and "Y" and "Y'" represent a hydroxyl group or Galβ1;

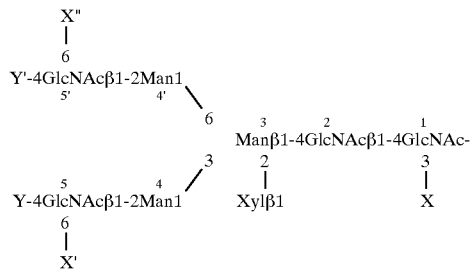

(5) Ultraviolet absorption spectrum
Exhibiting the maximum absorption spectrum at a wave length around 280 nm;

(6) Solubility in solvent
Soluble in water, physiological saline and phosphate buffer;

(7) Biological activity
Attaching to immunoglobulin E antibody collected from blood of a patient with pollenosis, and inducing pollenosis; and (8) Stability
Being inactivated in an aqueous solution of pH 7.2 when incubated at 100° C. for 10 minutes, and substantially not losing its activity in an aqueous solution at pH 7.2 even when allowed to stand at 4° C. for one month;

(9) Dynamics on MONO S Column
Absorbing on a column packed with MONO S and eluting therefrom with 10 mM Tris-HCl buffer of pH 7.0 containing 0.1–0.3M sodium chloride.

2. A desensitization agent comprising a pharmaceutically-acceptable carrier and an effective amount of a mixture of purified proteins selected from purified proteins having the following physicochemical properties as effective ingredients, said agent having an $LD_{50}$ of 1,000,000 ng or more when tested on a mouse independently of its administration route:

(1) Molecular weight
Exhibiting a band in a position corresponding to 44,000 to 54,000 daltons on sodium dodecylpolyacrylamide gel electrophoresis (SDS-PAGE):

(2) Isoelectric point (pI)
Exhibiting isoelectric points corresponding to 8.5 to 9.2 on isoelectrophoresis;

(3) Partial amino acid sequence containing the C-terminus Asn-Gly-Asn-Ala-Thr-Pro-Gln-Leu-Thr-Lys-Asn-Ala-Gly-Val-Leu-Thr-Cys-Ser-Leu-Ser-Lys-Arg-Cys (SEQ ID NO: 3);

(4) Sugar content
Containing sugar chains having a chemical structure in the molecule as shown by the following chemical formulae, where "X", "X'" and "X''" represent a hydroxyl group or Fucα1, and "Y" and "Y'" represent a hydroxyl group or Galβ1, and the removal of the sugar chain results in a significant reduction of antigenicity; Chemical Formula:

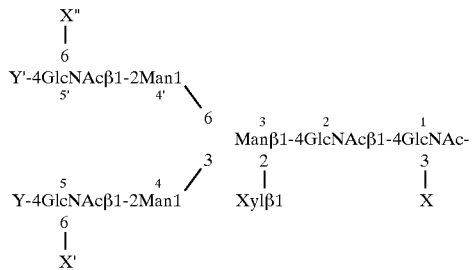

(5) Ultraviolet absorption spectrum
Exhibiting the maximum absorption spectrum at a wave length around 280 nm;

(6) Solubility in solvent
Soluble in water, physiological saline and phosphate buffer;

(7) Biological activity

Attaching to immunoglobulin E antibody collected from blood of a patient with pollenosis, and inducing pollenosis;

(8) Stability

Being inactivated in an aqueous solution of pH 7.2 when incubated at 100° C. for 10 minutes, and substantially not losing its activity in an aqueous solution of pH 7.2 when allowed to stand at 4° C. for one month, and (9) Dynamic on MONO S Column Absorbing on a column packed with MONO S and eluting therefrom with 10 mM Tris-HCl buffer of pH 7.0 containing 0.1–0.3M sodium chloride.

3. The desensitization agent in accordance with claim 2, wherein the purified protein is derived from a cedar pollen.

4. The desensitization agent in accordance with claim 2, wherein the purified protein is covalently attached to a saccharide.

5. The desensitization agent in accordance with claim 2, which contains as a stabilizer one or more members selected from the group consisting of serum albumin and gelatin.

6. The desensitization agent in accordance with claim 4, wherein the saccharide is one or more members selected from the group consisting of starch, amylose, dextran, polysurose, pullulan, elsinan, curdlan, gum arabic, gum tragacanth, guar gum, xanthan gum, carrageenan, cellulose, glucomannan, chitosan, lipopolysaccharides, and their derivatives and partial hydrolysates.

7. The desensitization agent in accordance with claim 6, wherein the saccharide has an average molecular weight in the range of about 500–10,000,000 daltons.

8. The desensitization agent in accordance with claim 4, wherein the weight ratio of the purified protein to the saccharide is about 1:0.001 to 1:1,000, on a dry solid basis.

9. The desensitization agent in accordance with claim 4, wherein the covalent attachment between the purified protein and the saccharide is formed by reacting them at a pH of about 0.1–12 and a temperature of about 0°–100° C. for about 0.1–50 hours.

10. A method for diagnosing pollenosis comprising scratching a patient on the skin;

dropping an effective amount of the desensitization agent according to claim 2 onto the scratched skin; and noting the occurrence and size of urtica formed 15–20 minutes after dropping the desensitization agent onto the scratched skin.

11. A method for diagnosing pollenosis comprising:

injecting a patient with an effective amount of the desensitization agent according to claim 2 to cause a reaction in a sensitive patient; and noting the occurrence and size of urtica formed 15–20 minutes after injecting the desensitization agent.

12. A method for treating a patient suffering from pollenosis comprising administering to said patient an effective amount of a desensitization agent according to claim 2.

13. The method according to claim 12 wherein said desensitization agent is administered at a dose of about 0.0001–100,000 ng/dose/adult.

14. The method according to claim 13 wherein said desensitization agent is administered at a dose of about 0.001–10,000 ng/dose/adult.

15. The method according to claim 12 wherein said desensitization agent is administered at a frequency of at least one dose per week for a period of for one to twelve months.

16. The method according to claim 12 wherein said desensitization agent is administered via a route selected from the group consisting of intradermal, subcutaneous, intramuscular, and permucosal administration at a dose of about 0.001–10,000 ng/dose/adult at a frequency of at least one dose per week for a period of for one to six months, during which time the dose is increased.

* * * * *